(12) United States Patent
Krolik et al.

(10) Patent No.: US 10,085,765 B2
(45) Date of Patent: Oct. 2, 2018

(54) APPARATUS AND METHODS FOR ACCESSING AND REMOVING MATERIAL FROM BODY LUMENS

(71) Applicant: Incept, Inc., Bedford, MA (US)

(72) Inventors: Jeffrey A. Krolik, Campbell, CA (US); James H. Dreher, Santa Monica, CA (US); Gwendolyn A. Watanabe, Wayne, PA (US)

(73) Assignee: Incept, Inc., Bedford, MA (US)

( * ) Notice: Subject to any disclaimer, the term of this patent is extended or adjusted under 35 U.S.C. 154(b) by 69 days.

(21) Appl. No.: 14/847,008

(22) Filed: Sep. 8, 2015

(65) Prior Publication Data

US 2015/0374404 A1    Dec. 31, 2015

Related U.S. Application Data

(60) Division of application No. 13/022,523, filed on Feb. 7, 2011, now Pat. No. 9,126,015, which is a
(Continued)

(51) Int. Cl.
*A61B 17/32* (2006.01)
*A61B 17/3207* (2006.01)
(Continued)

(52) U.S. Cl.
CPC ...... *A61B 17/320725* (2013.01); *A61B 17/22* (2013.01); *A61M 25/04* (2013.01);
(Continued)

(58) Field of Classification Search
CPC ...... A61B 17/320725; A61B 17/32075; A61B 17/320758; A61B 17/32002;
(Continued)

(56) References Cited

U.S. PATENT DOCUMENTS 4,299,226 A * 11/1981 Banka ................. A61M 25/104
                                                 600/434
4,744,366 A *  5/1988 Jang .................... A61M 25/1011
                                                 604/101.02
(Continued)

FOREIGN PATENT DOCUMENTS

DE   10 2005 021470 A1   11/2006
JP      H02-055064 A      2/1990
(Continued)

OTHER PUBLICATIONS

Final Office Action dated Jul. 22, 2014, as received in corresponding Japanese Patent Application No. 2011-522299, and an English language summary of the same.
(Continued)

*Primary Examiner* — Jocelin Tanner
(74) *Attorney, Agent, or Firm* — Baker Hostetler LLP

(57) ABSTRACT

An apparatus and method are provided for accessing and/or removing material from a body lumen. The apparatus includes a tubular sheath including a shaft having a proximal end and an expandable distal end that is expandable between a collapsed configuration and an expanded, tapered configuration. A treatment member can be introduced into the body lumen through the tubular sheath. The treatment member includes one or more expandable members to interact with the material to be removed from the body lumen.

20 Claims, 11 Drawing Sheets

Related U.S. Application Data continuation of application No. PCT/US2009/053237, filed on Aug. 8, 2009.

(60) Provisional application No. 61/087,508, filed on Aug. 8, 2008.

(51) Int. Cl.
| | |
|---|---|
| *A61B 17/22* | (2006.01) |
| *A61M 25/04* | (2006.01) |
| *A61M 25/09* | (2006.01) |
| *A61B 17/221* | (2006.01) |
| *A61M 25/10* | (2013.01) |

(52) U.S. Cl.
CPC ... *A61M 25/09* (2013.01); *A61B 2017/22001* (2013.01); *A61B 2017/2215* (2013.01); *A61B 2017/22054* (2013.01); *A61B 2017/22061* (2013.01); *A61B 2017/22067* (2013.01); *A61B 2017/22068* (2013.01); *A61B 2017/22069* (2013.01); *A61B 2017/22072* (2013.01); *A61B 2017/22079* (2013.01); *A61M 25/1002* (2013.01); *A61M 25/104* (2013.01)

(58) Field of Classification Search
CPC ...... A61B 17/320016; A61B 17/32056; A61B 17/3207; A61B 17/22; A61B 17/221; A61B 2017/320716; A61B 2017/320766; A61B 2017/320775; A61B 2017/320024; A61B 2017/320028; A61B 2017/22001; A61B 2017/22072; A61B 2017/22081; A61B 2017/22084; A61B 2017/2215; A61B 2017/22054; A61B 2017/22067; A61B 2017/22079; A61B 2017/22061; A61B 2017/22069; A61B 2017/22068; A61M 25/09; A61M 25/04; A61M 25/1002; A61M 25/104; A61M 2025/0024; A61M 2025/0025; A61M 25/0029

See application file for complete search history.

(56) References Cited

U.S. PATENT DOCUMENTS

| | | | |
|---|---|---|---|
| 4,921,478 A | 5/1990 | Solano et al. | |
| 5,201,756 A * | 4/1993 | Horzewski | A61M 25/0023 604/104 |
| 5,226,880 A | 7/1993 | Martin | |
| 5,318,588 A | 6/1994 | Horzewski et al. | |
| 5,531,719 A | 7/1996 | Takahashi | |
| 5,792,158 A | 8/1998 | Lary | |
| 5,833,650 A * | 11/1998 | Imran | A61M 25/1011 604/508 |
| 5,868,776 A * | 2/1999 | Wright | A61F 2/958 604/101.02 |
| 6,063,056 A | 5/2000 | Engelberg | |
| 6,106,540 A | 8/2000 | White et al. | |
| 6,287,271 B1 | 9/2001 | Dubrul et al. | |
| 6,540,712 B1 | 4/2003 | Parodi et al. | |
| 6,960,222 B2 * | 11/2005 | Vo | A61B 17/12 604/103.07 |
| 2002/0173815 A1 * | 11/2002 | Hogendijk | A61B 17/12 606/194 |
| 2003/0055449 A1 * | 3/2003 | Lee | A61F 2/95 606/194 |
| 2003/0109886 A1 | 6/2003 | Keegan et al. | |
| 2003/0163158 A1 | 8/2003 | White | |
| 2005/0125021 A1 * | 6/2005 | Nance | A61B 17/3417 606/192 |
| 2005/0288764 A1 * | 12/2005 | Snow | A61F 2/95 623/1.11 |
| 2006/0041228 A1 | 2/2006 | Vo et al. | |
| 2006/0085024 A1 | 4/2006 | Pepper et al. | |
| 2006/0224155 A1 | 10/2006 | Schmaltz | |
| 2007/0100424 A1 | 5/2007 | Chew et al. | |

FOREIGN PATENT DOCUMENTS

| | | |
|---|---|---|
| JP | 2000-005189 A | 1/2000 |
| JP | 2001-508635 A | 6/2001 |
| JP | 2003-521286 A | 7/2003 |
| JP | 2004-097807 A | 4/2004 |
| JP | 2007-504910 A | 3/2007 |
| JP | 2007-522881 A | 8/2007 |
| WO | WO2005079678 A1 | 9/2005 |

OTHER PUBLICATIONS

First Office Action dated Dec. 4, 2012, as received in corresponding Chinese Patent Application No. 200980138987.0, and an English language summary of the same.

Invitation to Respond to Written Opinion dated Oct. 24, 2012, as received in corresponding Singaporean Patent Application No. 201100870-3.

Notice of Rejection dated Aug. 20, 2013, as received in corresponding Japanese Patent Application No. 2011-522299, and an English language translation of the same.

Second Office Action dated Jun. 8, 2013, as received in corresponding Chinese Patent Application No. 200980138987.0, and an English language summary of the same.

International Search Report and Written Opinion dated Apr. 12, 2010, as received in corresponding International Application No. PCT/US2009/053237.

International Preliminary Report on Patentability dated Feb. 17, 2011, as received in corresponding International Application No. PCT/US2009/053237.

* cited by examiner

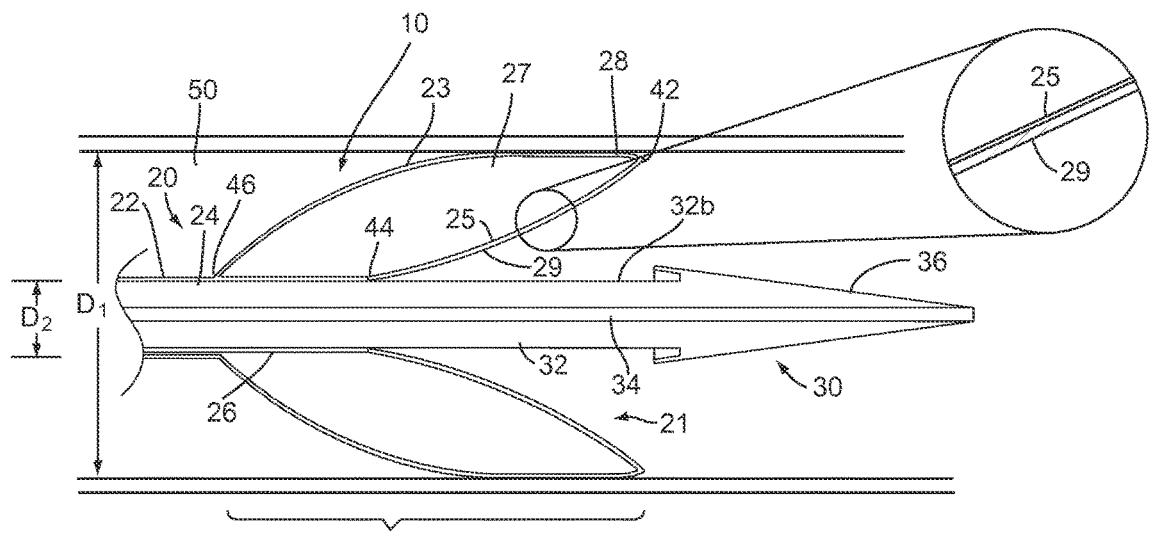
FIG. 2A
FIG. 2B
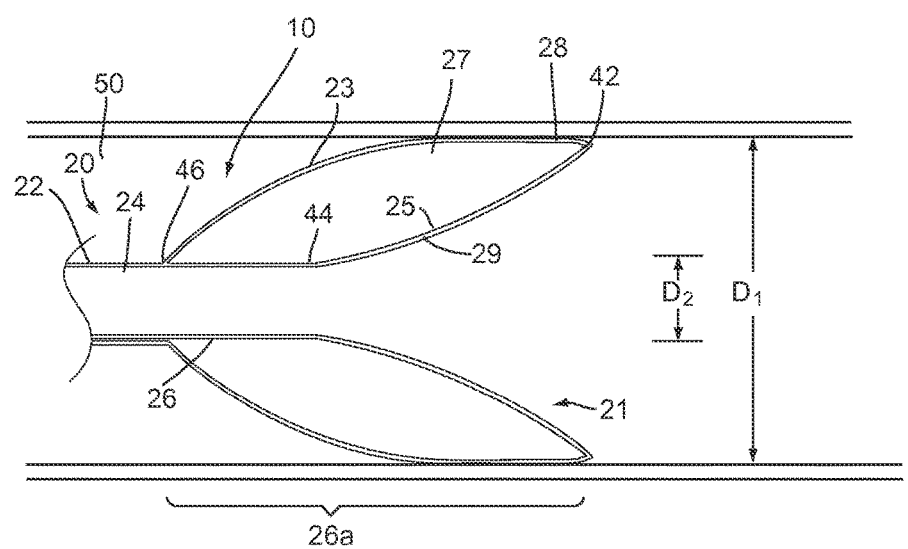
FIG. 3

APPARATUS AND METHODS FOR ACCESSING AND REMOVING MATERIAL FROM BODY LUMENS

RELATED APPLICATIONS

This application is a divisional of U.S. patent application Ser. No. 13/022,523, filed Feb. 7, 2011, which is a continuation of International Patent Application No. PCT/US2009/053237, filed Aug. 8, 2009, which claims the benefit of U.S. Provisional Patent Application No. 61/087,508, filed Aug. 8, 2008, the entire disclosures of which are expressly incorporated by reference herein.

FIELD OF THE INVENTION

The present invention relates generally to apparatus for treating obstructive material, e.g., thrombus, stenosis, and/or other obstructions within a body lumen of a patient, e.g., within a tubular graft, aorto-venous fistula, blood vessel, and the like. More particularly, the present invention relates to apparatus for removing or otherwise capturing thrombus or other obstructive material within a body lumen, and/or for dilating a body lumen, and to methods for making and using such apparatus.

BACKGROUND

Flow within a blood vessel or other body lumen within a patient's vasculature may become constricted or ultimately interrupted for a variety of reasons. For example, a vessel may gradually narrow due to inflammation and/or cell proliferation. In addition, thrombus may form due to such narrowing or other flow problems within a vessel.

For example, an aorto-venous graft may be implanted in an arm of a patient experiencing kidney failure, e.g., to facilitate dialysis treatment. Such grafts may be a fistula formed directly in the patient's body, e.g., through tissue between an adjacent artery and vein or other vessels, may be a xenograft implanted between two vessels, or may be a synthetic graft. Such grafts only have a limited life cycle due to inflammation, thrombus formation, and the like. Once such a graft becomes sufficiently occluded or otherwise deteriorates, a new graft must be implanted at a new location for subsequent treatment.

Accordingly, apparatus and methods for removing material from aorto-venous grafts, blood vessels, or other body lumens and/or otherwise treating body lumens would be useful.

SUMMARY

The present invention is directed to apparatus for treating a body lumen of a patient, e.g., a tubular graft, aorto-venous fistula, blood vessel, and the like. More particularly, the present invention is directed to apparatus for removing or otherwise capturing thrombus or other obstructive material within a body lumen, and/or for dilating a body lumen, and to methods for making and using such apparatus.

In accordance with one embodiment, a system is provided for removing obstructive material from a body lumen that includes an elongate tubular member including a proximal end, a distal end sized for introduction into a body lumen, a lumen extending between the proximal and distal ends, and an elongate treatment member insertable through the lumen and including an expandable treatment element selectively expandable for treating one or more regions within a body lumen. For example, the treatment element may be used to direct obstructive material into the tubular member lumen.

In an exemplary embodiment, the tubular member may include an annular expandable member on the distal end that is expandable from a collapsed configuration to an expanded configuration wherein the expandable member adopts a tapered shape that flares outwardly away from the distal end to define an inlet that is larger than and communicates with the lumen, the expandable member sized to engage a wall of a body lumen within which the expandable member is expanded.

For example, the expandable member may include an outer annular membrane surrounding an inner annular membrane, the outer and inner membranes being attached together and to the tubular member distal end such that the outer and inner membranes together define a substantially enclosed interior. The tubular member may include an inflation lumen communicating with the interior such that, when inflation media is delivered via the inflation lumen into the interior, the expandable member is expanded to the expanded configuration.

In an exemplary embodiment, the outer membrane may have a greater axial length than the inner member such that proximal ends of the outer and inner membranes are spaced apart from one another along the distal end of the tubular member. For example, the proximal end of the outer membrane may be attached to the distal end of the tubular member at a first location and the proximal end of the inner membrane may be attached to the distal end of the tubular member at a second location distal to the first location.

In addition or alternatively, the inner membrane may be more resistant to bending or compression than the outer membrane. For example, the inner membrane may include a reinforcement layer to increase the resistance of the inner membrane to bending or compression.

Optionally, the tubular member may include an access port on the proximal end providing access to the lumen for removing material therefrom.

In another option, the system may include one or more additional components. For example, a dilator may be disposed within the lumen of the tubular member such that a tapered distal tip extends beyond the expandable member in the collapsed configuration to provide a substantially smooth transition during introduction of the tubular member into a body lumen. In an exemplary embodiment, the dilator may include a recess adjacent the distal tip for receiving a distal end of the expandable member in the collapsed configuration. The dilator may be removable proximally from the tubular member lumen after the tubular member is introduced into a body lumen such that the treatment device may be inserted into the tubular member lumen.

Optionally, the tubular member may include an expandable section including at least the distal end that is expandable from a relaxed size to an enlarged size to accommodate receiving material larger than the relaxed state directed into the lumen by the treatment device. For example, the tubular member may be expandable along the entire length between the proximal and distal ends.

In an exemplary embodiment, the expandable section of the tubular member may include an elastic layer coupled to an inelastic layer including one or more slots therein to accommodate the inelastic layer expanding, the elastic layer biasing the expandable section to return towards the relaxed size. For example, the elastic layer may include an elastic sleeve surrounding the inelastic layer. In addition or alternatively, the inelastic layer may include a tubular body and wherein the one or more slots comprise one or more longitudinal slots extending along the length of the tubular body. Alternatively, the inelastic layer may include a tubular body and the one or more slots may include a plurality of longitudinal slots spaced apart axially and circumferentially from one another along the length of the tubular body.

In any of these embodiments, the treatment element of the treatment device may include a first non-compliant balloon mounted on a distal end of the treatment device. In addition or alternatively, a second compliant balloon may be mounted on treatment device, e.g., over the first balloon.

In addition or alternatively, the treatment device comprises a traction member at least partially covering the treatment element. For example, the fraction member may be movable between a first position wherein the traction member is disposed adjacent the treatment element and a second position wherein the fraction member at least partially covers the treatment element. In an exemplary embodiment, the traction member may include an expandable mesh.

In accordance with another embodiment, an apparatus is provided for providing access to a body lumen that includes an elongate tubular member comprising a proximal end, a distal end sized for introduction into a body lumen, and a lumen extending between the proximal and distal ends; and an annular expandable member on the distal end that is expandable from a collapsed configuration to an expanded configuration wherein the expandable member adopts a tapered shape that flares outwardly away from the distal end to define an inlet that is larger than and communicates with the lumen, the expandable member sized to engage a wall of a body lumen within which the expandable member is expanded.

In accordance with yet another embodiment, an apparatus is provided for removing obstructive material from a body lumen and for dilating the body lumen. For example, the apparatus may include an outer tubular member having a proximal end, an expandable distal end, and a first lumen extending between the proximal and distal ends. The apparatus may also include an inner member comprising a proximal end and a distal end having a tapered profile, wherein the inner member is configured for being slidably disposed within the first lumen of the outer member such that the inner member proximal end extends proximally from the outer member proximal end and the inner member distal end extends distally from the outer member distal end. Optionally, the inner member may have an undercut configured for engaging the outer member distal end when the outer member distal end is in an unexpanded configuration. In addition or alternatively, the apparatus may include an elongate member configured for being slidably disposed within the first lumen of the outer member. The elongate member may include two concentric balloons on a distal end thereof, wherein one of the balloons is more compliant than the other balloon. For example, the less compliant balloon may be configured for dilating the body lumen.

In one embodiment, the distal end of the outer member may include an inner membrane, an outer membrane, and a cavity between the inner and outer membranes. Optionally, the inner membrane may include a reinforcement layer that allows radial expansion and resists bending and/or compression in an axial direction. The inner membrane may have a shorter length than the outer membrane or they may have similar lengths. The outer member may further include a second lumen extending between the outer member proximal and distal ends and communicating with the cavity.

The outer member expandable distal end may have an expanded configuration wherein a distal opening of the outer member has a first diameter, and the distal end tapers from the first diameter proximally towards a second diameter, wherein the first diameter is larger than the second diameter. For example, the first diameter may be adjustable such that the distal opening may be substantially equal to an inner diameter of a body lumen within which the expandable distal end is expanded.

In accordance with still another embodiment, an apparatus is provided for treating a body lumen. The apparatus includes an tubular sheath having a proximal end, an expandable distal end having an expanded configuration and an unexpanded configuration, a shaft extending between the proximal and distal ends, and a first lumen extending between the proximal end and a distal opening in the distal end, wherein, when the distal end is in the expanded configuration, the distal end tapers from a first diameter at the distal opening to a second diameter of the shaft, wherein the first diameter is larger than the second diameter.

Optionally, the apparatus may also include a dilator slidably disposed within the first lumen of the sheath. The dilator includes a proximal end adjacent the sheath proximal end, a distal end extending from the sheath distal end and having a tapered distal tip, and an annular region adjacent the distal tip for receiving the sheath distal end when the sheath distal end is in the unexpanded configuration, e.g., to provide a substantially smooth transition between the distal tip and the sheath.

In accordance with yet another embodiment, an apparatus for treating a body lumen is provided that includes a tubular member including a proximal end, an expandable distal end, a first lumen extending between the proximal and distal ends, and a second inflation lumen extending between the proximal and distal ends, wherein the distal end, in an expanded configuration, has a tapered profile that tapers from a first diameter at a distal opening proximally towards a second diameter, wherein the first diameter is greater than the second diameter.

In one embodiment, the tubular member distal end may include an inner membrane, an outer membrane, and a cavity between the inner membrane and the outer membrane, and the second lumen may communicate between the cavity and an inflation port on the tubular member proximal end. Optionally, the inner membrane may include a reinforcement layer. The reinforcement layer may be formed of a material that is resistant to bending and/or compression in an axial direction relative to the tubular member. In addition or alternatively, the outer membrane may have a length that is greater than a length of the inner membrane or the lengths may be substantially the same. For example, when the tubular member distal end is in the expanded configuration, the inner membrane may have a concave configuration and the outer membrane may have a convex configuration.

Optionally, the apparatus may also include an inner member slidably disposed within the first lumen of the tubular member. The inner member includes a proximal end adjacent the tubular member proximal end, and a distal end extending from the tubular member distal end and having a tapered distal tip. The inner member distal end may include an annular undercut having an opening facing towards the inner member proximal end, wherein the tubular member distal end, in an unexpanded configuration, may fit within the opening.

In addition or alternatively, the apparatus may further include an elongate member configured for being slidably disposed within the tubular member first lumen. The elongate member may include one or more expandable members on a distal end thereof, e.g., a single balloon or concentric balloons, e.g., where the outer balloon is more compliant than the inner balloon.

In accordance with another embodiment, a method for treating a body lumen is provided that includes introducing a flow restoration apparatus into the body lumen, wherein the flow restoration apparatus comprises an outer member and an inner member disposed within a lumen of the outer member; expanding a distal end of the outer member from an unexpanded profile to a tapered, expanded profile, e.g., such that the outer member distal end engages or otherwise contacts an inner wall of the body lumen; and withdrawing the inner member from the outer member, thereby leaving the outer member in the expanded configuration disposed within the body lumen.

A procedure may then be performed via the outer member, e.g., to remove or otherwise treat obstructive material within the body lumen. For example, an elongate treatment member may be introduced through the outer member and into the body lumen and manipulated to capture or remove material within the body lumen. In one embodiment, a distal end of the treatment member may be advanced from the expanded distal end of the outer member and beyond material to be removed. A first expandable member on the treatment member distal end may be expanded, and the treatment member may be withdrawn towards the outer member to direct material in the body lumen into the outer member expanded distal end, e.g., by pulling the expanded first expandable member entirely into the outer member. Optionally, an additional obstruction within a portion of the body lumen may be located, and a second expandable member on the treatment member distal end may be expanded to dilate the portion of the body lumen.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIG. 2A is a cross-sectional view of the apparatus of FIG. 1A, showing an expandable member on the sheath in an expanded configuration within the body lumen.

FIG. 2B is a detail of a wall of the expandable member shown in FIG. 2A.

FIG. 3 is a cross-sectional view of the apparatus of FIGS. 1A and 2A with the expandable member in the expanded configuration and the dilator removed.

DETAILED DESCRIPTION OF THE EXEMPLARY EMBODIMENTS

Figure 7:
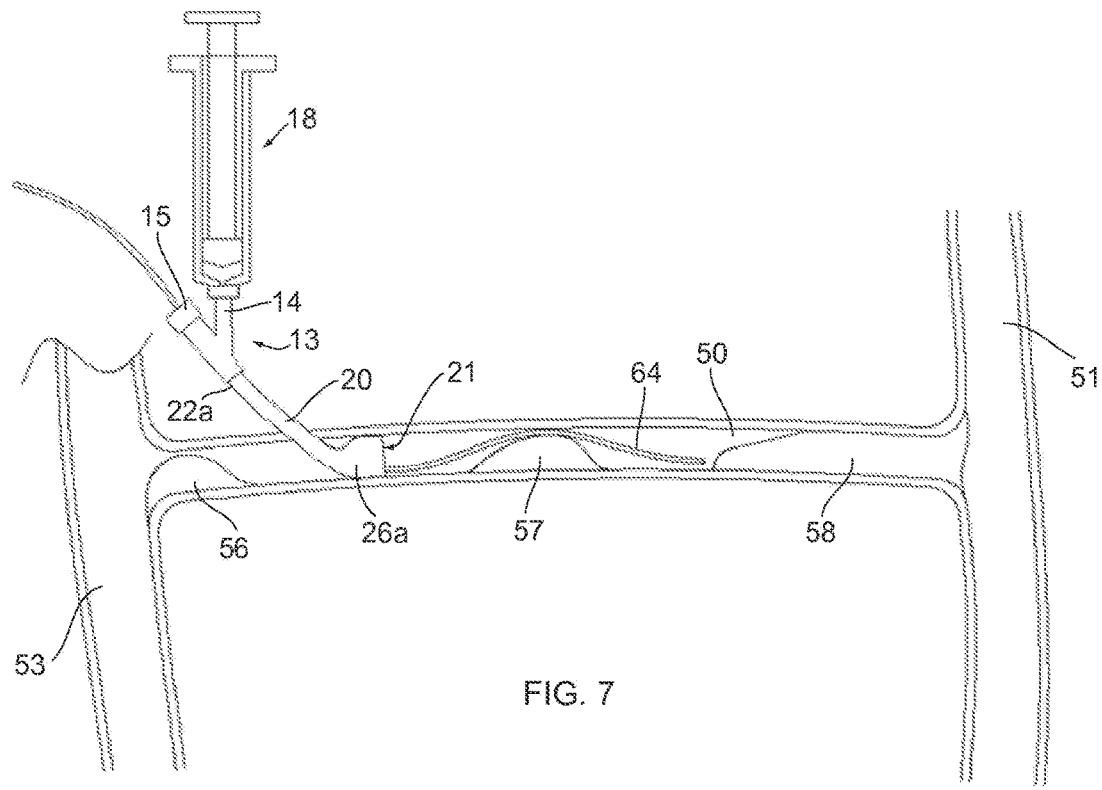

Turning to the drawings, FIGS. 1A-3 show a flow restoration apparatus 10 for providing access and/or treating a body lumen 50, e.g., for removing thrombus, objects, debris, and/or obstructive material from within the body lumen 50, and/or for dilating region of the body lumen 50, e.g., a blood vessel, aorto-venous fistula, tubular graft, and the like. Generally, the apparatus 10 includes an outer sheath or other tubular member 20, and, optionally, a dilator or other inner member 30, which together with one or more treatment apparatus (not shown), described further below, may provide a system for removing obstructive material and/or otherwise treating occluded regions within body lumens in a patient's body. In addition, such a system may include one or more additional components, e.g., one or more guidewires, syringes or other sources of inflation media and/or vacuum, and the like, such as guidewire 64 and syringe 18, as shown in FIG. 7 and described further below.

Figure 1A:
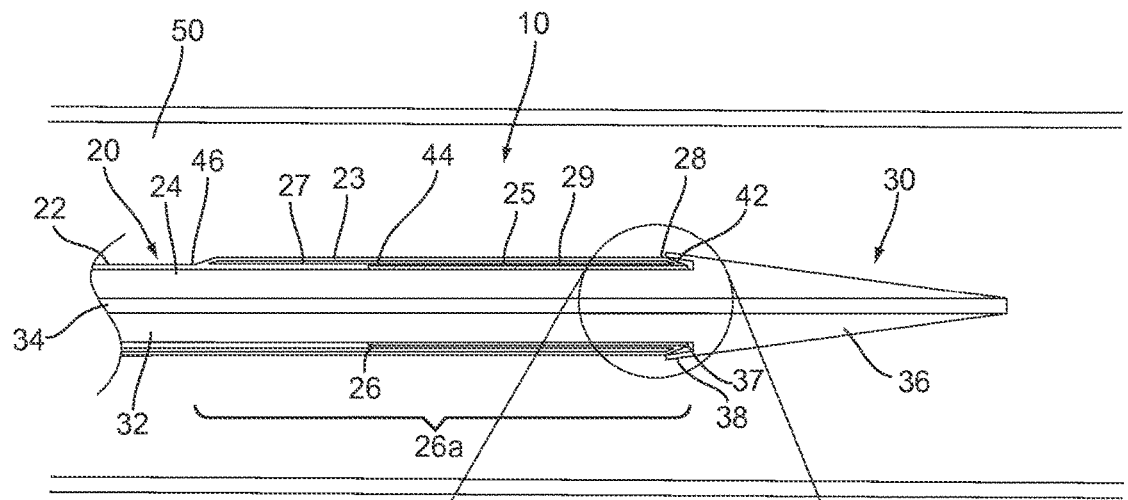
FIG. 1A is a cross-sectional view of a first exemplary embodiment of a flow restoration apparatus or system, including an outer sheath and a dilator, disposed within a body lumen.
Figure 1B:
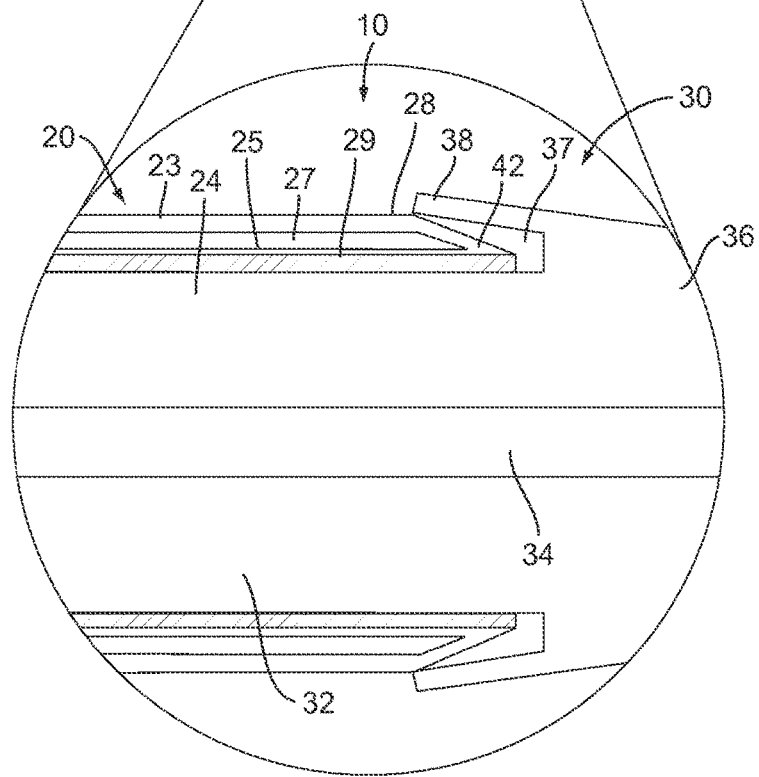
FIG. 1B is a detail of a distal portion of the apparatus shown in FIG. 1A.

With additional reference to FIGS. 6-9, the sheath 20 is an elongate tubular body or shaft 22 including a proximal end 22a, a distal end 26, and a lumen 24 (best seen in FIGS. 1A-3) extending therebetween. The distal end 26 may be expandable, i.e., movable between a collapsed configuration (as shown in FIGS. 1A and 1B) and an expanded configuration (as shown in FIGS. 2A and 3), e.g., in which the expandable distal end 26 has a tapered profile or transition. In the embodiment shown, the distal end 26 includes a balloon or other expandable member 26a attached to and/or extending from the distal end 26 of the shaft 22 to provide an expandable transition, as described further below.

Optionally, a handle or hub 13 may be coupled to or otherwise provided on the proximal end 22a of the sheath 20, e.g., for manipulating the sheath 20 and/or the entire apparatus 10. The handle 13 may have an ergonomic shape, e.g., to facilitate holding and/or manipulating the handle 13. The handle 13 may include one or more ports, e.g., side port 14, for coupling one or more fluid sources to the apparatus 10, such as a source of inflation media, a source of vacuum, and/or a source of diagnostic and/or therapeutic agents (not shown). The side port 14 may include one or more connectors (not shown) to facilitate coupling one or more sources of fluid to the side port 14, e.g., a Luer lock connector, and/or one or more seals, e.g., a hemostatic seal, to prevent fluid from leaking from the side port 64. In addition, the handle 13 may include a port 15 communicating with the lumen 24, e.g., for receiving the dilator 30, a guidewire or other device (not shown) into and/or through the lumen 24. The port 15 may include one or more seals, e.g., a hemostatic seal (not shown), to accommodate passage of the dilator 30 or other device therethrough without risk of substantial risk of leakage of blood or other body fluids from the lumen 24.

The sheath 20 may have a substantially uniform construction along its length, or alternatively, the construction may be varied. For example, a proximal portion of the sheath 20 may be substantially rigid or semi-rigid to facilitate advancement of the apparatus 10 by pushing or otherwise manipulating the proximal end 22a. In addition or alternatively, a distal portion of the sheath 20 may be flexible, e.g., to facilitate bending and/or advancement through tortuous anatomy without substantial risk of kinking or buckling. In exemplary embodiments, the sheath 20 may be formed from materials such as metal, plastic, e.g., PEEK, Grilamed L25, and the like, or composite materials. The sheath 20 may have a length between about five and one hundred thirty centimeters (5-130 cm) and an outer diameter between about 1.6 to 2.0 millimeters, and the lumen 24 may have a diameter between about 1.4 and 1.8 millimeters.

Returning to FIGS. 1A-3, the dilator 30 may be removably disposed within the lumen 24 of the sheath 20, and generally includes a shaft 32 including a proximal end 32a (not shown, see FIG. 6), a distal end 32b terminating in a tapered distal tip 36, and an accessory lumen 34 extending the proximal and distal ends 32a, 32b. The distal tip 36 may provide a substantially atraumatic transition for facilitating introduction of the apparatus 10 through skin, vessel walls, and other tissues and/or advancement within a body lumen. The tapered distal tip 36 may also provide a smooth transition between a guidewire and the outer sheath 20. The shaft 32 of the dilator 30, although flexible to accommodate bending, may be more rigid than the shaft 22 of the sheath 20 such that the dilator 30 may provide columnar support to the sheath 20 as it is advanced during introduction or subsequent manipulation.

As best seen in FIGS. 1A and 1B, the distal tip 36 of the dilator 30 extends distally from the distal end 26 of the sheath 20. The distal tip 36 of the dilator 30 may include an annular undercut or other region 38 at the proximal end of the distal tip 36, thereby defining an opening or recess 37 that faces towards the proximal end 32a of the dilator 30. When the dilator 30 is disposed within the lumen 24 of the sheath 20 and the expandable member 26a is in its collapsed configuration, a distal end 28 of the expandable member 26a may be received in the recess 37, as shown in FIGS. 1A and 1B. In this manner, the region 38 may provide a substantially smooth transition between the dilator 30 and the sheath 20 for facilitating passage of the apparatus 10 through tissue. The region 38 may also retain the expandable member 26a against the dilator 30, e.g., to prevent proximal migration of the expandable member 26a during advancement, which may otherwise cause the expandable member 26a to bunch up or compress axially.

In the embodiment shown in FIGS. 1A-3, the expandable member 26a includes an outer annular membrane or surface 23 and an inner annular membrane or surface 25 together defining a substantially enclosed interior or region 27 therebetween. A lumen (not shown) may extend from the inflation port 14 on the handle 13 through the proximal end 22a (not shown, see FIGS. 6-9) of the sheath 20 to the distal end 26 of the sheath 20, e.g., along a wall thereof, that communicates with the interior 27. As shown in FIGS. 6-9, a source of inflation media or vacuum, e.g., a syringe 18, may be coupled to the inflation port 14, such that the interior 27 of the expandable member 26a may be in fluid communication with the source 18a to allow inflation media, e.g., saline, water, and the like, to be delivered into and evacuated from the interior 27 of the expandable member 26a.

The outer and inner membranes 23, 25 may be formed from a single sheet or multiple sheets of material that may be bonded or otherwise attached together into annular sleeves, e.g., by bonding with adhesive, sonic welding, heat fusing, and the like, to substantially seal and/or enclose the interior 27. Alternatively, the outer and inner membranes 23, 25 may be formed as sleeves, e.g., by extrusion, injection molding, and the like. In the embodiment best seen in FIG. 1B, the outer and inner membranes 23, 25 may be formed as separate sleeves of material whose proximal and distal edges are attached together and/or to the distal end 26 of the sheath 20 to define the expandable member 26a. The membranes 23, 25 may be formed from substantially inelastic or non-compliant materials, e.g., such that the expandable member 26a expands to a predetermined size and/or shape upon inflation.

For example, the outer and inner membranes 23, 25 may be attached together at a distal bond location 42 (best seen in FIG. 1B) and attached to the distal end 26 of the shaft 22 at proximal bond locations 44, 46, respectively (best seen in FIGS. 1A and 2). For example distal edges of the outer and inner membranes 23, 25 may be lapped or butted together. The proximal edge of the outer membrane 23 may be attached to an outer surface of the shaft 22, while the proximal edge of the inner membrane 25 may be attached to an outer surface of the shaft 22, to an inner surface of the first lumen 24, or butted to the distal end 26.

As shown in FIGS. 1A and 2A, the proximal bond locations 44, 46 may be spaced apart axially from one another, although alternatively, the proximal edges of the outer and inner membranes 23, 25 may be attached to the distal end 26 at the same or similar axial locations, e.g., with the outer membrane 23 attached over the inner membrane 25. In the collapsed configuration, the outer and inner membranes 23, 25 may extend substantially axially with the outer membrane 23 substantially surrounding the inner membrane 25.

As shown in FIGS. 1A and 2, the outer membrane proximal bond location 46 is further from the distal end 28 of the expandable member 26a than the inner membrane proximal bond location 44. This may promote a desired shape for the expandable member 26a in the expanded configuration, e.g., providing a substantially continuous tapered internal diameter communicating with the lumen 24 of the sheath 20, as shown in FIG. 2A. For example, the tapered expanded profile may be due to the outer membrane 23 having a longer chord length between its proximal and distal bonding locations 46, 42 than that of the inner membrane 25. Upon inflation, the greater chord length of the outer membrane 23 may generate greater tension in the outer membrane 23 than in the inner membrane 25 with its shorter chord length. To balance these tensions, the expandable member 26a of the sheath 20 may expand radially outwardly in a curved or conical shape to reduce the tension in the outer membrane 23. Thus, when the expandable member 26a is expanded to the expanded configuration, the diameter of the inner membrane 25 (the inner diameter of the expandable member 26a) may taper from a relatively large distal diameter $D_1$ at distal opening 21 to a relatively small proximal diameter, $D_2$. The material and size of the expandable member 26a may be selected such that the relatively large distal diameter $D_1$ is substantially equal to or greater the inner diameter of a body lumen 50 within which the apparatus 10 is introduced, as explained further below.

The expandable member 26a of the sheath 20 may be expanded by introducing inflation media into the interior 27 defined by the outer and inner membranes 23, 25. FIG. 2A shows the apparatus 10 after the expandable member 26a has been fully inflated. During the balloon inflation, the distal end 28 of the expandable member 26a may flare radially outwardly away from a central longitudinal axis of the sheath 20 and become free from the recess 38 in the dilator 30. The inflation pressure may exert a tension on the outer membrane 23 that causes it to expand away from the longitudinal axis of the sheath 20. Tension may also be exerted on the distal bond location 42 and proximal bond locations 44, 46. The proximal bond locations 44, 46 do not undergo a substantial shape change in response to the applied tension because they are bonded to the sheath shaft 22, which does not allow radial expansion. The distal bond location 42 is pulled by the tension on the outer membrane 23 in a radially outward direction as the expandable member 26a expands to the expanded configuration.

To further enhance the expandable member 26a adopting a tapered shape in the expanded configuration, different materials may be provided for the outer and inner membranes 23, 25. For example, the inner membrane 25 may be more rigid than the outer membrane 23, e.g., by providing a different relatively stiff material, a similar but greater thickness material, and the like for the inner membrane 25. Optionally, as shown in FIG. 2B, the inner membrane 25 may include a reinforcement layer 29 to create or enhance adoption of the tapered shape. For example, strips of material (not shown), e.g., hard plastic such as nylon or PEEK, or metal, such as stainless steel or Nitinol, may be bonded, embedded, or otherwise attached to the inner membrane 25 such that the strips extend substantially axially at least partially between the proximal and distal bond locations 44, 42. Alternatively, a braid or other mesh (not shown) may be embedded within or attached to an inner or outer surface of the inner membrane 25. The reinforcement layer 29 may be substantially uniform or different along the axial length of the inner membrane 25. For example, the reinforcement layer 29 may increase the rigidity of the inner membrane 25 adjacent the proximal bond 44 relative to the region adjacent the distal bond 42, if desired, e.g. to enhance the inner membrane 25 expanded into a bell shape during expansion of the expandable member 26a.

In addition or alternatively, the material of the reinforcement layer 29 may allow radial expansion, while resisting bending or compression of the inner membrane 25 axially relative to the longitudinal axis of the sheath 20. For example, the combination of the reinforcement layer 29 and the proximal bond locations 44, 46 may cause the expandable member 26a to adopt a pointed oval or almond shape in cross-section in the expanded configuration, as shown in FIGS. 2A and 3. For example, the inner membrane 25 may have define a bell shape, e.g., having a concave cross-section, or may have a substantially straight conical shape when the inner membrane 25 flares or tapers. The tapered shape of the expandable member 26a may be advantageous for removing debris from a body lumen 50 because of the resulting relatively large diameter inlet 21 that may funnel material into a relatively small lumen 24 for removal from the body lumen, as described further below.

Once the expandable member 26a is expanded and the distal end 28 leaves the recess 37 of the dilator 30, the dilator 30 is free to be withdrawn proximally from the sheath 20. The expanded sheath 20 with the dilator 30 removed is shown in FIG. 3. Thrombus and other unwanted materials within a body lumen 50 within which the sheath 20 is deployed may then be swept into the lumen 24 of the sheath 20 via the tapered inlet 21, as described in more detail below.

For example, turning to FIGS. 4-10, the apparatus 10 may be used to provide access and/or removing thrombus or other material within or adjacent a dialysis or other tubular graft. Although the method of using the apparatus 10 is shown and described below as taking place within a tubular graft, the apparatus 10 is not restricted to use within such a graft and may be used other body lumens within a patient's body, such as an aorto-venous fistula, xenograft, blood vessel, and the like.

Figure 4:
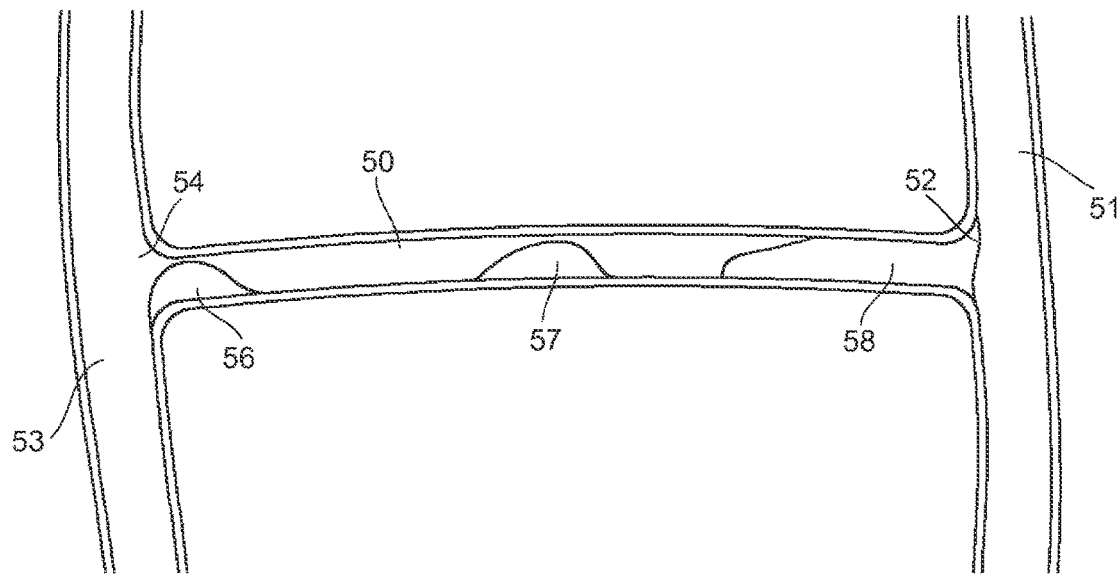
FIG. 4 is a cross-sectional view of a patient's body showing an exemplary dialysis graft extending between a vein and an artery, and including obstruction material within the graft lumen.

An exemplary graft lumen 50 is shown in FIG. 4, which extends between an artery 51 and a vein 53, e.g., within a patient's arm or other location within a patient's body. Thus, the graft lumen 50 may connect to the arterial blood flow through an arterial anastomosis 52, and to the venous blood flow through a venous anastomosis 54. As is common in dialysis graft failures, FIG. 4 shows that the venous anastomosis 54 is narrowed due to the presence of a stenosis 56, which may be caused by inflammation and cell proliferation (also known as neointimal hyperplasia). A second stenosis 57 is shown in the mid-graft area. Additionally, a thrombus 58 is shown formed at the arterial anastomosis 52, e.g., due to the slowed blood flow through the graft lumen 50 as a result of the stenoses 56, 57 present.

Figure 5:
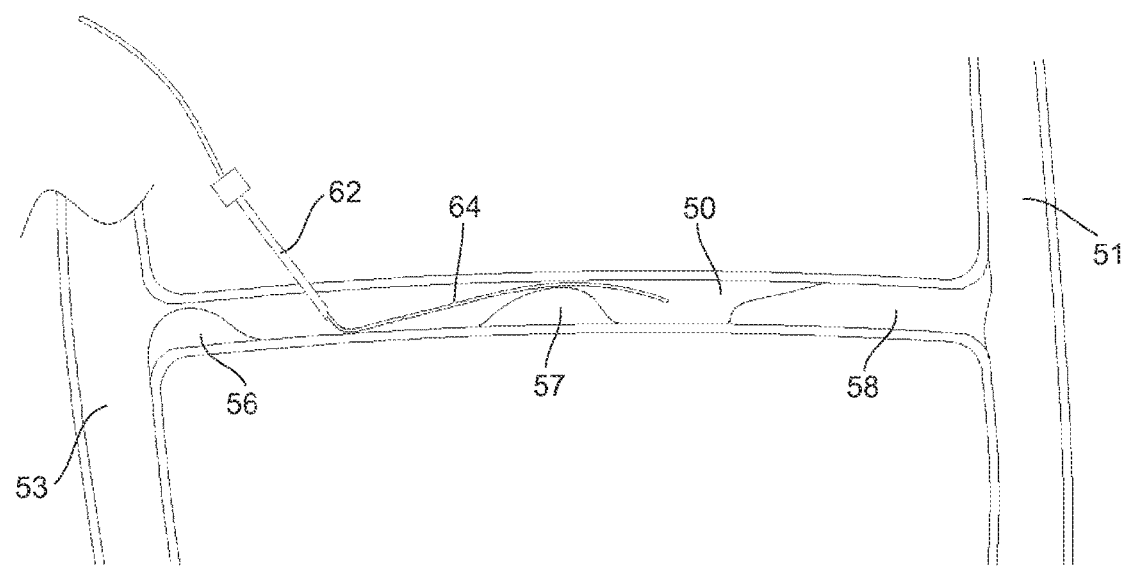
FIGS. 5-10 are a cross-sectional views of the dialysis graft of FIG. 4, showing an exemplary method of removing obstructive material from the graft lumen.

Initially, as shown in FIG. 5, a needle 62 may be inserted through the patient's skin and into the graft lumen 50. A guidewire 64 may then be advanced through the needle 62 and into the graft lumen 50 for some distance, e.g., to provide mechanical stability during subsequent instrument introduction.

Figure 6:
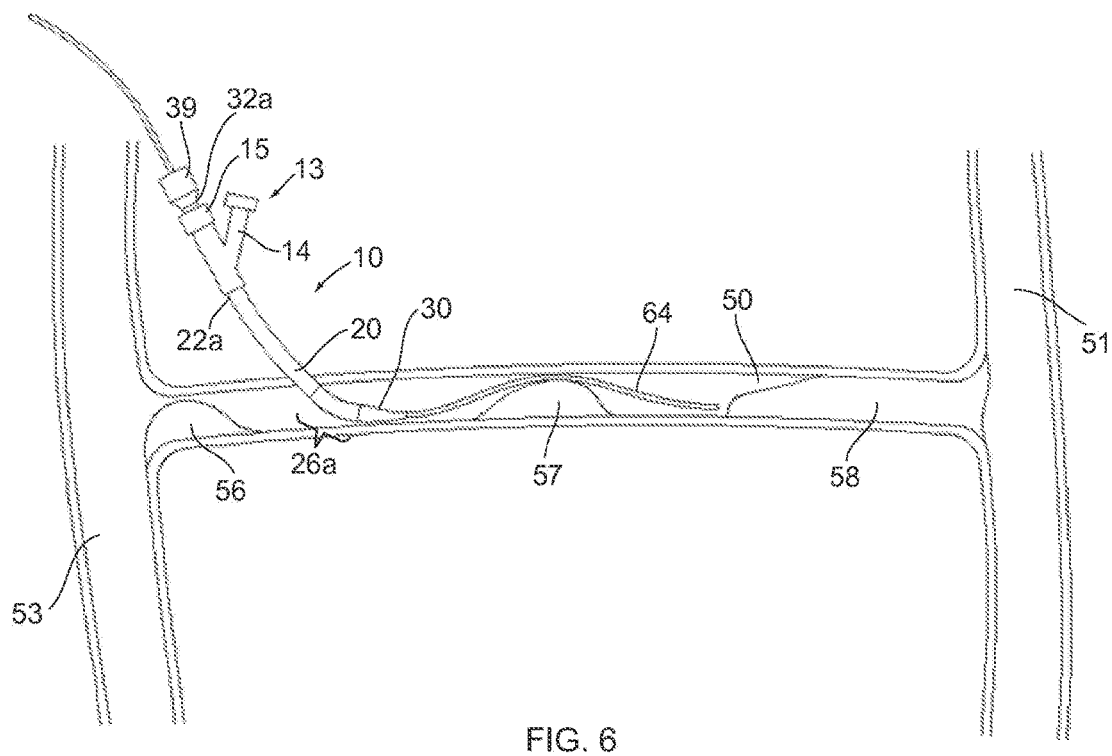

Next, as shown in FIG. 6, the apparatus 10 may be introduced over the guidewire 64 and into the graft lumen 50. The apparatus 10 may be provided from the manufacturer with the dilator 30 loaded into the sheath 20, as shown in FIGS. 1A and 6. Alternatively, the dilator 30 may be loaded into the sheath 20, e.g., by inserting the distal tip 36 into the port 15 immediately before the procedure. In this alternative, the dilator 30 may be advanced such that the distal tip 36 passes beyond the distal end 28 of the expandable member 26a, and the dilator 30 may be withdrawn to capture the distal end 28 in the recess 37. In another alternative, the annular region 38 and recess 37 may be omitted from the dilator 30 and the dilator 30 may simply pass through and extend beyond the expandable member 26a and distal end 26 of the sheath 20.

With the apparatus 10 assembled, the guidewire 64 may be backloaded through the distal tip 36 of the dilator 30 into the accessory lumen 34 and out the proximal hub 39. The apparatus 10 may then be advanced over the guidewire 64 through the skin and any intervening tissue into the graft lumen 50 with the expandable member 26a in the collapsed configuration until the expandable member 26a is received completely in the graft lumen 50, as shown in FIG. 6. Optionally, the dilator 30 and/or expandable member 26a may include one or more markers (not shown), e.g., one or more radiopaque bands or other markers, such that external imaging, e.g., fluoroscopy, x-ray imaging, ultrasound, and the like may be used to position the expandable member 26a to a desired position within the graft lumen 50.

Turning to FIG. 7, with the sheath 20 in a desired position within the graft lumen 50, the distal end 26 of the sheath 20 may be expanded. With the distal end 28 of the expandable member 26a removed from the region 37, the dilator 30 may be removed from the graft lumen 50 and sheath 20. Alternatively, if the dilator 30 does not include the annular region 38 and recess 37, the dilator 30 may be removed before the expandable member 26a is expanded.

As shown in FIG. 7, a syringe 18 may be coupled to the inflation port 14 to expand the distal end 26 of the sheath 20 via an inflation lumen (not shown) within the wall of the sheath 20 that allows fluid communication with the interior 27 (shown in FIGS. 1A-3) of the expandable member 26a.

The expandable distal end 26a of the sheath 20 may provide several advantages over existing non-expanding sheaths. First, because the expanded diameter $D_1$ of the distal end 26 is substantially equal to or greater than the inner diameter of the graft lumen 50, the expanded expandable member 26a may form a seal with the graft lumen 50, thereby preventing blood flow and lowering the chances of embolization of thrombus or other particles to the rest of the body during the procedure. Second, the gradual tapered internal diameter of the expandable member 26a may facilitate removal of material from the graft lumen 50 by providing a funnel or gradual, smooth taper. Third, the expandable member 26a may substantially stabilize the sheath 20 within the graft lumen 50 by the traction between the expandable member 26a and the wall of the graft lumen 50, e.g., to prevent undesired migration of the sheath 20 during the procedure.

Figure 8:
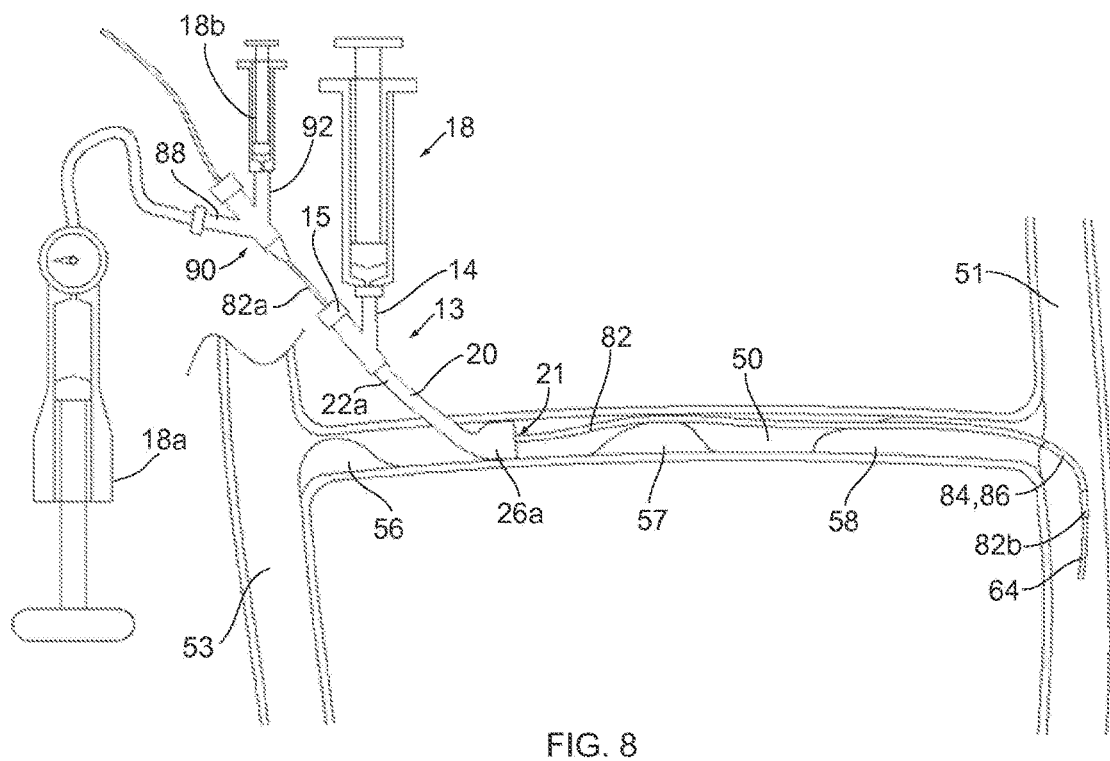

Next, as shown in FIG. 8, with the expandable member 26a of the sheath 20 expanded and the dilator 30 removed, one or more treatment devices may be introduced via the sheath 20 into the graft lumen 50, e.g., to perform one or more diagnostic and/or therapeutic procedures.

As shown in FIG. 8, a balloon catheter 82 may be inserted over the guidewire 64 and through the lumen 24 of the sheath 20, into the graft lumen 50, e.g., to a position on the far side of the material forming stenosis 57 and thrombus 58. The catheter 82 may include a guidewire lumen (not shown) extending between a proximal hub or handle 90 on a proximal end 82a of the catheter 82 and a distal end 82b of the catheter 82, i.e., for use as an over-the-wire system (shown). Alternatively, the guidewire lumen in the catheter 82 may extend from the distal end 82b to an intermediate location (not shown), e.g., for use as a rapid-exchange system.

Figure 14A:
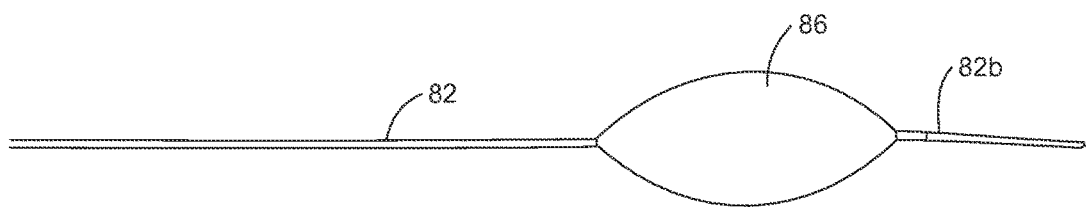
FIG. 14A is a side view of an alternative embodiment of a balloon catheter that may be used in the methods shown in FIGS. 5-12.

In one embodiment, the balloon catheter 82 may be a low-pressure embolectomy catheter, e.g., including a compliant balloon on the distal end 82b, e.g., as shown in FIG. 14A. However, in the exemplary embodiment shown in FIG. 8, the balloon catheter 82 may include multiple balloons or expandable members to provide a multiple purpose device. For example, as shown, two concentric balloons 84, 86 may be provided on the distal end 82b of the balloon catheter 82. A first, non-compliant, high pressure balloon 84 may be bonded or otherwise attached to the shaft of the catheter 82. The non-compliant balloon 84 may be in independent fluid communication with a first inflation port 88 on the hub 90, e.g., to which a syringe or other source of inflation media 18a may be coupled. A second, compliant, low-pressure balloon 86 may be bonded concentrically over the non-compliant balloon 84. The compliant balloon 86 may be in independent fluid communication with a second inflation port 92 on the catheter hub 90, e.g., to which a syringe or other source of inflation 18b may be coupled.

Figure 9:
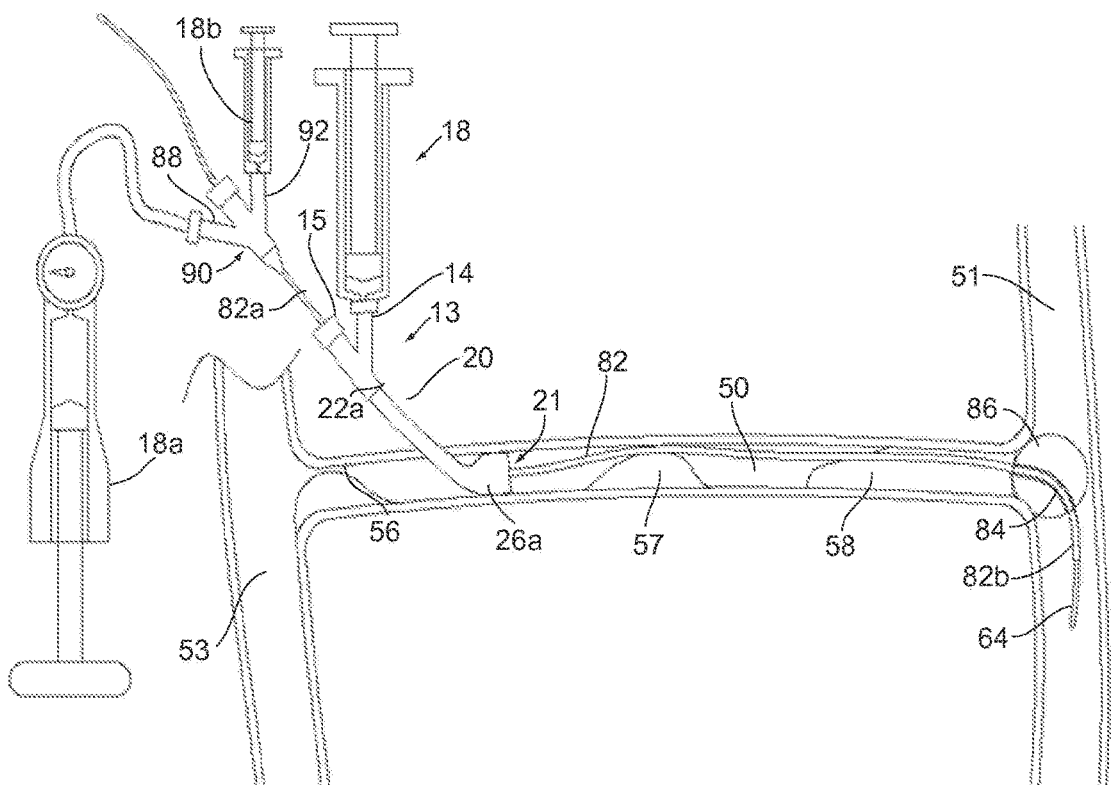

Turning to FIG. 9, with the catheter 82 in place with the distal end 82b within the artery 51 or otherwise beyond the thrombus 58, the compliant balloon 86 may be expanded. The fluid and obstructive material (e.g., stenosis 57 and thrombus 58) within the graft lumen 50 may thus be substantially isolated between the sheath 20 and the compliant balloon 86, e.g., substantially reducing the chance of material being embolized into the artery 51, vein 53 and/or elsewhere in the body.

Figure 10:
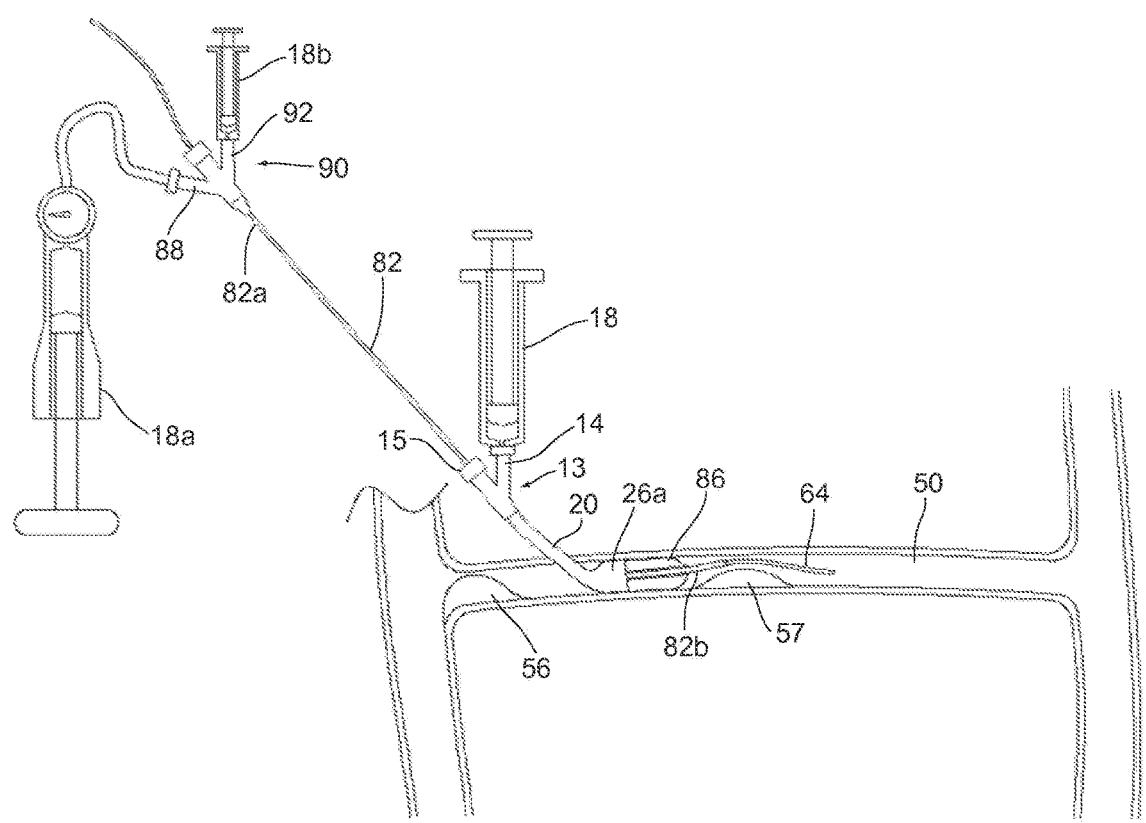

As shown in FIG. 10, the balloon catheter 82 may then be retracted proximally towards the sheath 20, pulling thrombus or other obstructive material with it. Optionally, the balloon catheter 82 may be pulled completely into and through the sheath 20, e.g., to substantially reduce the risk of the material becoming lodged in or otherwise occluding the sheath lumen 24.

All of the unwanted material may not be removed in a single pass of the compliant balloon 86. For example, as shown in FIG. 10, a portion of the mid-graft stenosis 57 may remain attached to the lumen wall. For this reason, multiple passes may be completed, e.g., collapsing the compliant balloon 86, advancing the balloon catheter 82, expanding the compliant balloon 86, and pulling the balloon catheter 86 one or more additional times, as desired. Optionally, any stenosis, thrombus, or other debris (e.g., stenosis 56) that was not reachable due to the orientation of the sheath 20 towards the artery 51 may be removed by removing the apparatus 10 and introducing the apparatus 10 (or another new apparatus with a dilator placed within a sheath, not shown) in the opposite direction within the graft lumen 50.

Some obstructions such as the mid-graft stenosis 57, shown in FIG. 10, may not completely removed by the compliant balloon 86. To address any stenosis that does not respond to balloon embolectomy, a high pressure dilation of the stenosis may be performed, as discussed in further detail with reference to FIGS. 11-12. The apparatus 10 along with the dual-balloon catheter 82 may offer an improved method of performing dilation because of the dual balloon construction.

Figure 11:
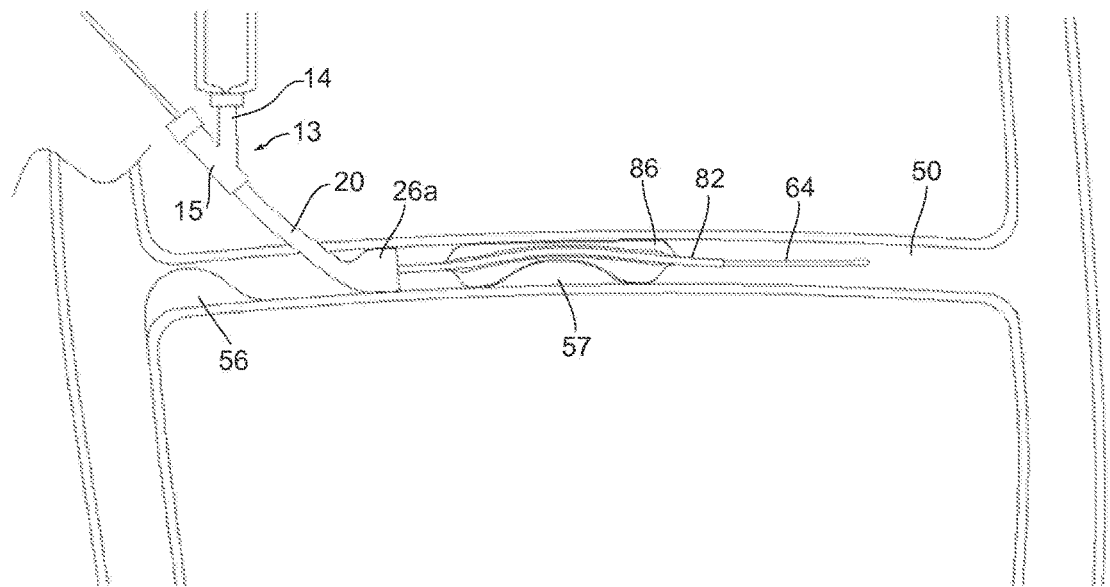
FIGS. 11-12 are cross-sectional views of the dialysis graft of FIG. 4, showing a method for dilating an occluded region of the graft.

First, as shown in FIG. 11, the compliant balloon 86 may be inflated with a contrast solution and moved axially within the lumen 50. When the balloon 86 encounters the stenosis 57, it deforms to adopt the shape of the stenosis 57, as shown, which may be visible via fluoroscopy or other external imaging. In addition, when the compliant balloon 86 encounters the stenosis 57 during retraction, a greater resistance may be felt than when moving the balloon 86 in an unobstructed vessel, giving the user tactile feedback as well as or instead of the external imaging. Thus, using visual and/or tactile feedback, the compliant balloon 86 may be accurately positioned over the stenosis 57, as shown in FIG. 11.

Figure 12:
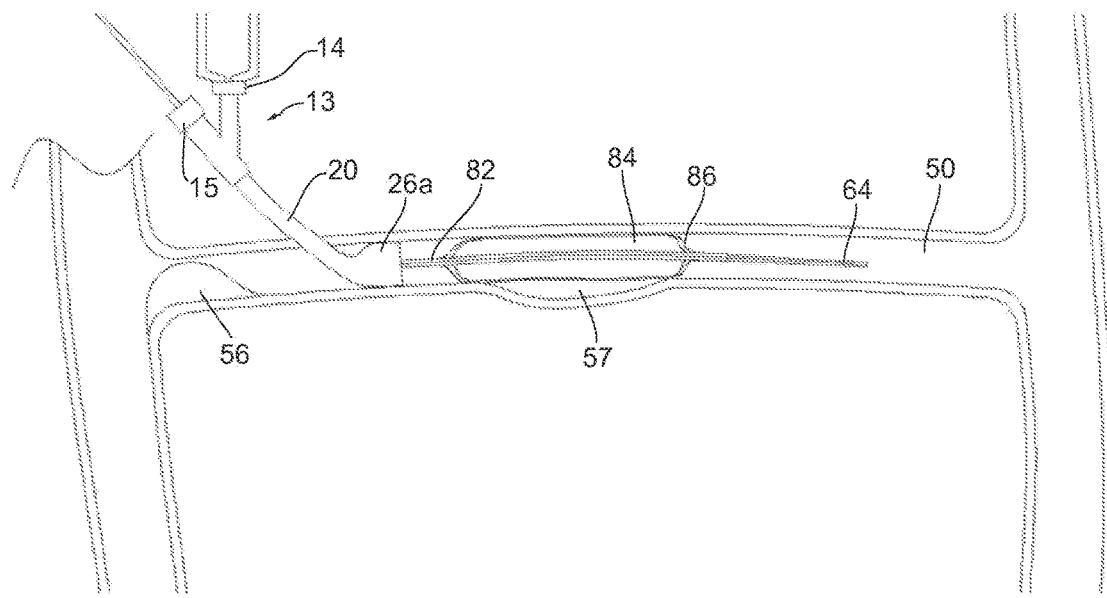

Turning to FIG. 12, with the balloon catheter 82 in the position identified using the compliant balloon 86, the non-compliant balloon 84 may then be inflated to dilate the stenosis 57. The compliant balloon 86 may deflated substantially simultaneously with inflation of the non-compliant balloon 84 or immediately before inflation. Thus, the stenosis 57 may be dilated, as shown, leaving a substantially unobstructed graft lumen 50.

One of the advantages of this dilation procedure over conventional dilation procedures is that that the stenosis 57 may easily and directly be located using the same catheter 82 that will be used for dilation, thereby eliminating catheter exchanges otherwise needed to replace the balloons. Another advantage is that no contrast solution is released into the bloodstream of the patient during this dilation procedure. Many patients have problems tolerating contrast solutions, especially those patients with compromised kidney function, and therefore may benefit from the dilation procedure described above.

In further alternatives, other devices may be introduced using the apparatus 10, e.g., to perform a procedure within the graft lumen 50 or at other locations within a patient's body where the sheath 20 is deployed. Exemplary apparatus and methods that may be used are disclosed in application Ser. Nos. 61/099,171, filed Sep. 22, 2008, 61/143,603, filed Jan. 9, 2009, 61/152,227, filed Feb. 12, 2009, Ser. No. 12/480,664, filed Jun. 8, 2009, Ser. No. 12/497,135, filed Jul. 2, 2009, and in International Publication No. WO 2009/076482. The entire disclosures of these references are expressly incorporated by reference herein.

Figure 13:
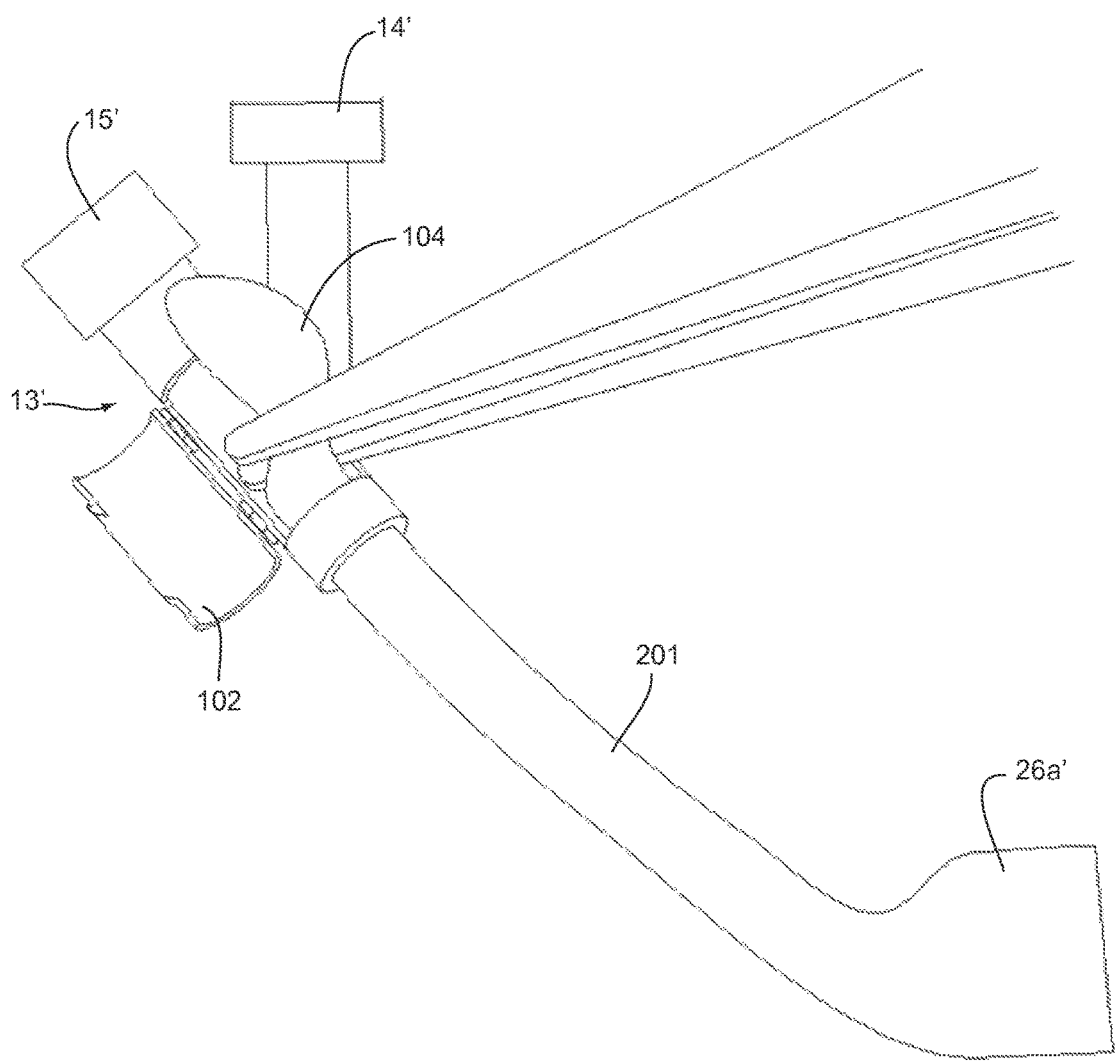
FIG. 13 is a perspective view of an alternative embodiment of a sheath that may be included in the flow restoration apparatus and methods of FIGS. 1A-12.

During removal of stenosis or thrombus, e.g., using any of the apparatus and methods described herein, it may be desirable to unclog or prevent clogging of the sheath. To facilitate this, it may be desirable to provide an access port into the proximal end of the sheath. Turning to FIG. 13, a sheath 20' is shown, which may be similar to that shown in FIGS. 1A-3 and described elsewhere herein, which may include a door 102 in its handle 13.' The door 102 may be opened by a user, e.g., at any time during a procedure, so that thrombus or other material 104 drawn into the sheath 20' may be manually removed from the handle 13,' e.g., if the sheath 20 becomes clogged. Alternatively, other types of repeatably openable and closeable access ports or structures may be provided instead of the door 102, e.g., a breach or other slidable mechanism (not shown), which may provided on the handle 13' or elsewhere on the sheath 20.' In a further alternative, the handle 13' may have a compartment (not shown) into which material (e.g., thrombus 104) may be pushed, e.g., when the material is withdrawn proximally through the sheath 20,' e.g., using the balloon 86 of the balloon catheter 82 or other device described herein.

Figure 14B:
FIGS. 14B-14D are side views of another alternative embodiment of the balloon catheter shown in FIG. 14A.
Figure 14C:
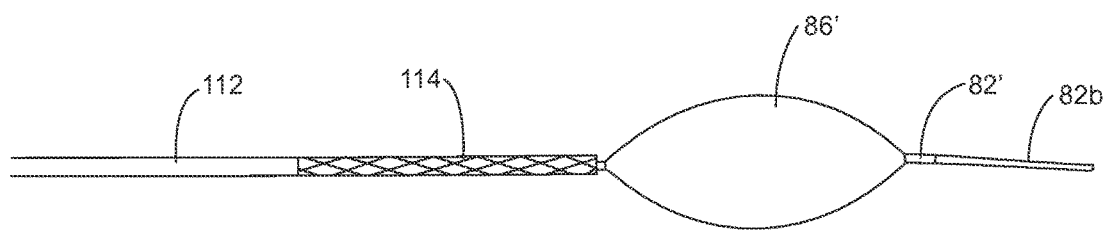
Figure 14D:
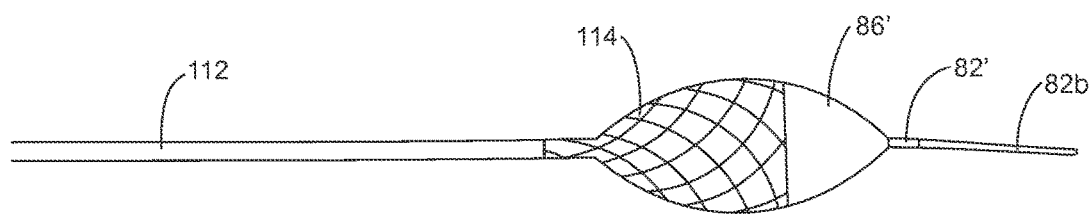

Turning to FIGS. 14B-14D, another embodiment of a treatment device is shown that may be included with the apparatus 10 to provide a system for treating a body lumen. In this embodiment, a balloon catheter 82' is shown that may be introduced through the sheath 20 (not shown, see FIGS. 1A-3) to remove thrombus or other material from a graft or other body lumen. For example, FIG. 14A shows a balloon catheter 82 including a compliant balloon 86 having a smooth outer surface, which may limit the ability of the balloon 86 to remove materials that are adherent to a wall of a body lumen.

To increase traction, as shown in FIGS. 14B-14D, a balloon catheter 82' may be provided that includes a compliant, low pressure balloon 86' and a traction sheath 112. The balloon 86' may be provided on a distal end 82b' of the catheter 82,' similar to other embodiments herein, and the traction sheath 112 may be received concentrically over the catheter 82' and/or over the balloon 86.' In the embodiment shown, the traction sheath 112 includes a tubular body carrying an expandable mesh 114 on its distal end. The traction sheath 112 may be movable axially relative to the catheter 82,' e.g., such that the expandable mesh 114 may selectively surround at least a portion of the balloon 86.' Initially, during a procedure, the expandable mesh 114 may be provided adjacent to the balloon 86,' i.e., without covering any portion of the balloon 86.'

If the balloon 86' alone does not remove sufficient thrombus or other material from a body lumen, as desired, the traction of the balloon 86' may be increased by advancing the traction sheath 112 from a first position proximal to the balloon 86,' as shown in FIG. 14C, to a second position wherein the mesh 114 is disposed at least partially over the balloon 86,' as shown in FIG. 14D. The balloon catheter 82' may include an actuator on its proximal end (not shown) for directing the traction sheath 112 between the first and second positions. Alternatively, the actuator may allow the traction sheath 112 to be directed to multiple positions, e.g., to cover the balloon 86' with as much of the expandable mesh 114 as desired. In a further alternative, the fraction sheath 112 may be attached or fixed to the catheter 82' such that the expandable mesh 114 covers a predetermined portion of the balloon 86.'

The mesh 114 may provide a rough surface that may be pushed into or otherwise enhance engagement with material to be removed from the body lumen using the inflated balloon 86.' Furthermore, the amount of tension that may be applied to the traction sheath 112 may be higher than that of the balloon 86' alone, because the traction sheath 112 is constructed of thicker and/or stronger materials than the compliant balloon 86.' The mesh 114 on the traction sheath 112 may be constructed of a variety of materials, including a hollow braid of metal or polymer strands, a polymer or metal tube cut with a plurality of apertures to form a stent-like structure, or a series of longitudinal struts composed of metal or plastic that remain substantially parallel to each other during their initial advancement over the balloon 86.'

Figure 15A:
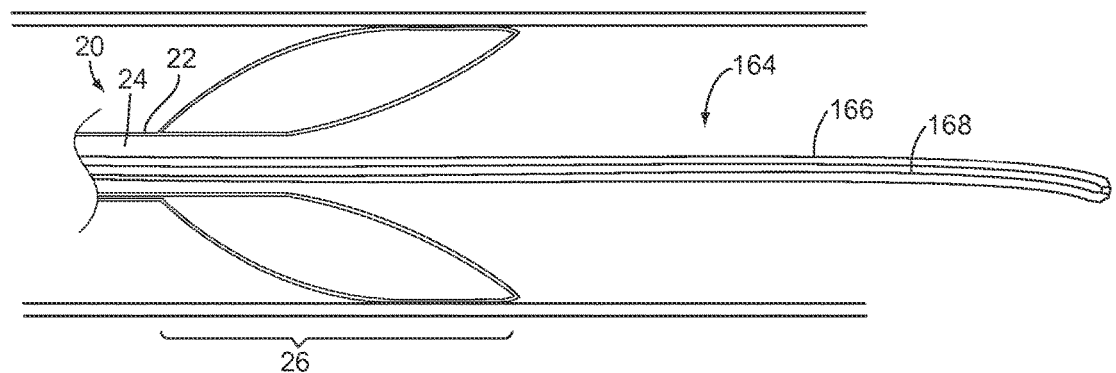
FIGS. 15A and 15B are cross-sectional views of a second exemplary embodiment of a flow restoration apparatus including an outer sheath and a guidewire.
Figure 15B:
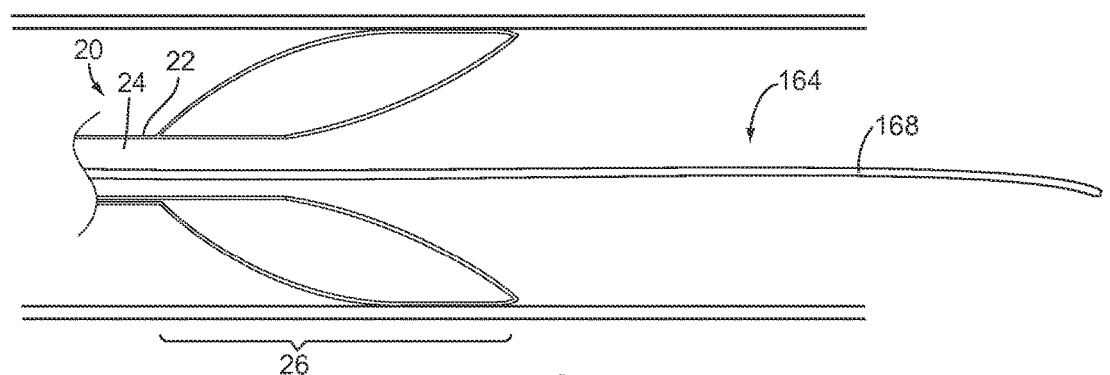

Turning to FIGS. 15A and 15B, a sheath 20 is shown that includes a lumen 24 and an expandable member 26a, similar to the other embodiments herein. As will be appreciated, the lumen 24 of the sheath 20 must accommodate a guidewire, a treatment device, such as balloon catheter 82 (not shown), as well as material being captured or removed using the treatment device. Given that these devices occupy space within the lumen 24, the sheath 20 may be limited in how large the particles are that the sheath is able to receive. FIGS. 15A and 15B show an alternative embodiment of a guidewire 164 that may be used in conjunction with the sheath 20 and/or apparatus 10 (not shown), which may be any of the embodiments described herein. Thus, the guidewire 164 may be included as part of a system including the apparatus 10 and/or any of the treatment devices described herein or in the references incorporated by reference herein.

In one embodiment for maximizing the ability of the sheath 20 to remove large particles, the space that the guidewire occupies within the lumen 24 of the sheath 20 may be minimized. Relatively larger guidewires (e.g., approximately 0.035 inches in diameter) are commonly used due to their high levels of support for devices tracked over them. FIG. 15A shows an alternative embodiment of a guidewire 164 over which a sheath 20 has been advanced. The guidewire 164 includes an inner portion or core 168 over which an outer portion or sleeve 166 is slidably disposed. With the sleeve 166 positioned over the core 168, the guidewire 164 may have properties similar to other guidewire, e.g., allowing the guidewire 164 to be introduced easily through a needle or other instrument into a graft lumen 50 or other body lumen, e.g., similar to the process shown in FIG. 5. Once the guidewire 164 is positioned sufficiently into the graft lumen 50, an apparatus 10 (not shown) including sheath 20 may be advanced over the guidewire and into the graft lumen 50, similar to the embodiments shown in FIGS. 6 and 7. If desired, the guidewire 164 may be manipulated further if not already positioned, e.g., such that the distal end of the guidewire 164 extends beyond thrombus or other material to be removed or treated, e.g., as shown in FIG. 8.

Once the sheath 20 and guidewire 164 are in place, the sleeve 166 of the guidewire 164 may be removed, leaving behind the relatively small diameter core 168 of the guidewire 164, as shown in FIG. 15B. This smaller guidewire 168 occupies less space inside the lumen 24 of the sheath 20 and, thereby allows larger particles to be drawn into the lumen 24, e.g., using an embolectomy balloon catheter or other treatment device, such as those described elsewhere herein. In this embodiment, the treatment device may have a relatively small accessory lumen to slidably accommodate the core 168 of the guidewire 164 therein, and therefore the shaft of the treatment device may also have a relatively small outer diameter compared to a device that is advanced over a larger guidewire. Thus, the smaller guidewire 164 and consequent treatment device shafts may leave more room within the lumen 24 to remove larger particles from of the body lumen.

Figure 16A:
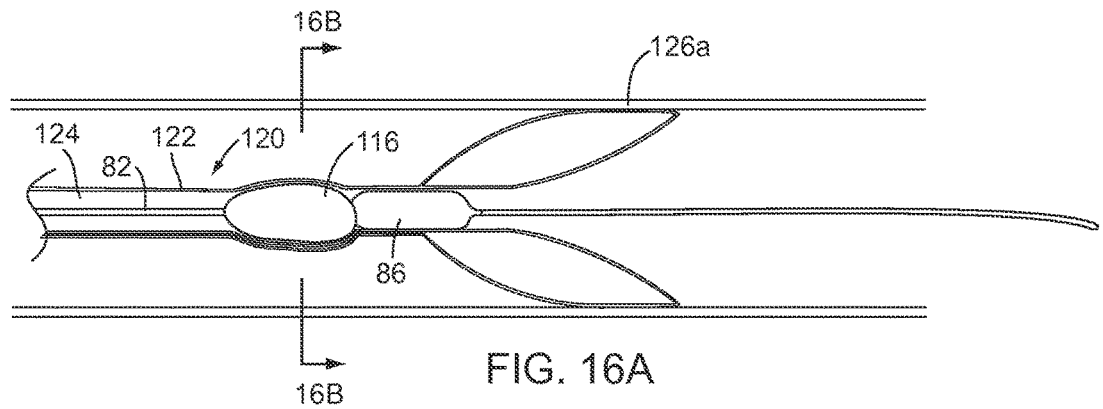
FIG. 16A is a cross-sectional view of a third embodiment of a flow restoration apparatus including an outer sheath carrying an expandable member and having an expandable wall, and a balloon catheter.
Figure 16B:
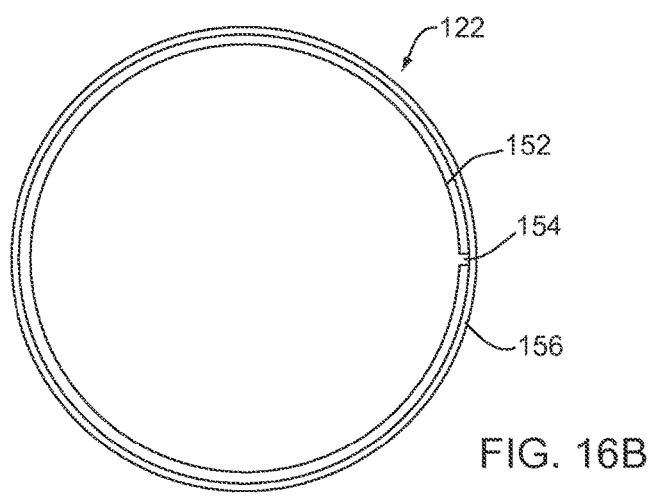
FIG. 16B is a cross-section of the sheath of FIG. 16A taken along line 16B-16B.
Figure 16C:
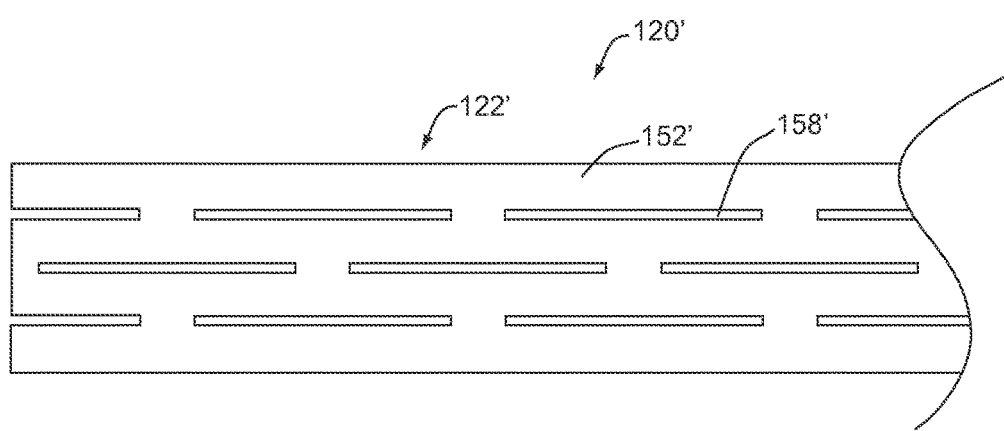
FIG. 16C is a detail of an alternative embodiment of the sheath of FIG. 16A, including slots for providing an expandable wall.

Turning to FIGS. 16A-16C, another embodiment of a sheath 120 is shown that may increase the ability of the sheath 20 to remove relatively large particles. Generally, the sheath 120 may include features similar to the other embodiments described herein, and may be incorporated into the apparatus 10 shown in FIGS. 1A-3 or any other apparatus or system. For example, the sheath 120 includes a shaft 122 carrying an expandable member 126a, which may be constructed and used similar to the previous embodiments.

Unlike the previous embodiments, at least a portion of the shaft 122 of the sheath 120 may be radially expandable to accommodate a relatively large particle 116 passing therethrough, as shown in FIG. 16A. In this example, an embolectomy balloon 86 is being used to pull the particle 116 through the sheath lumen 24 and out of a body lumen and a patient's body.

As shown in more detail in FIG. 16B, the shaft 122 of the sheath 120 may include an inner layer 152 constructed from one or more substantially inelastic material, e.g., for providing desired structural rigidity to the sheath 120. One or more slots 154 may be provided in the inner layer 152, e.g., extending along the entire length of the sheath 120 or only along a distal portion of the sheath 120, for example, if the sheath 120 include a relatively large diameter proximal portion. The shaft 122 also includes an outer shaft layer 156, which may be constructed from one or more elastic materials that provide a fluid-tight outer skin for the shaft 122, e.g., to prevent fluid from passing through the slot(s) 154 in the inner layer 152. If a radially-outward force is applied, e.g., the slot(s) 154 may open and the outer layer 156 may elastically deform to allow radial expansion of the shaft 122. When the radially-outward force is removed, the outer layer 156 may resiliently return inwardly to the original size, closing the slot(s) 154.

As shown, the outer layer 156 may be an enclosed sleeve surrounding the inner layer 152. The outer layer 156 may be attached to the inner layer 152, e.g., to an outer surface of the inner layer 152, for example, by interference fit, by bonding with adhesive, sonic welding, heat fusing, and the like. Alternatively, the elastic layer 156 may be bonded to the inside diameter of the inelastic layer 152 (not shown), which may provide a harder and/or more lubricious outer surface for the sheath 120, if desired. In an alternative embodiment, the elastic layer may be bonded to an inside surface of the slotted layer.

During use, a treatment device, such as balloon catheter 82 shown in FIG. 16A may be used to draw thrombus or other material 116 into the lumen 124 of the sheath 120, similar to the previous embodiments. If the material 116 is larger than the diameter of the lumen 124 with the outer layer 156 in its relaxed or relatively low potential energy state, then pulling the material 116 into the lumen 124 may cause the outer layer 156 to stretch, thereby opening the slot(s) 154 and increasing the diameter of the inner layer 152 and shaft 122. As the material 116 passes along the expandable portion of the shaft 122, the shaft 122 may resiliently expand and contract back towards the relaxed state, as can be seen in FIG. 16A.

Turning to FIG. 16C, another embodiment of a sheath 120' is shown (with an expandable member not shown merely for convenience) that includes an alternative radially expandable shaft 122'. Instead of one or more elongated slots along the entire length of expandable portion of the shaft 122,' a plurality of discrete length slots 158' may be provided in a relatively inelastic layer 152,' e.g., similar to a slotted-tube stent. An elastic layer (not shown) may again be provided on the outside or inside of the inelastic layer 152.' The slots 158' may be formed in the wall of the inelastic layer 152,' e.g., by cutting the slots 158' into a tube, e.g., by laser cutting, mechanical cutting, or by cutting the slots in a sheet and rolling and attaching longitudinal edges of the sheet (not shown). The material of the inelastic layer 152' may be sufficiently flexible to accommodate deformation of the inelastic layer 152,' e.g., such that radial expansion of the shaft 122' may occur similarly to the opening of a stent as oversized material is pulled through the lumen 124.' The elastic layer may resiliently bias the inelastic layer 152' and consequently the shaft 122' to return inwardly towards the relaxed or smaller diameter.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for treating a body lumen, the method comprising:
   introducing a guidewire into a body lumen;
   introducing a flow restoration apparatus over the guidewire into the body lumen, the flow restoration apparatus comprising an outer member having a shaft defining a first lumen, and an inner member disposed within the first lumen of the outer member, the shaft having a distal end configured to radially expand, a distal end of the inner member extending distally of the distal end of the outer member;
   expanding the distal end of the outer member from a collapsed configuration to a tapered, expanded configuration while the inner member is within the first lumen of the outer member, such that a diameter of a distal opening of the outer member is substantially equal to an inner diameter of the body lumen;
   withdrawing the inner member from the first lumen of the outer member, thereby leaving the outer member with its distal end in the expanded configuration disposed within the body lumen;
   introducing a treatment member through the first lumen of the outer member and into the body lumen such that material within the body lumen is positioned between a distal end of the treatment member and the expanded distal end of the outer member;

expanding a first expandable member on the treatment member distal end; and withdrawing the treatment member into the first lumen of the outer member such that the material in the body lumen is also withdrawn into the first lumen of the outer member, the withdrawal of the material in the body lumen causing radial expansion of the shaft.

2. The method of claim 1, further comprising:
locating an additional obstruction within a portion of the body lumen;
expanding a second expandable member on the treatment member distal end to dilate the portion of the body lumen; and
withdrawing the treatment member and the outer member from the body lumen.

3. The method of claim 2, wherein the first expandable member is disposed concentrically around the second expandable member, the method further comprising contracting the first expandable member before or substantially simultaneously with expanding the second expandable member.

4. The method of claim 2, wherein locating the additional obstruction within the portion of the body lumen comprises:
introducing the treatment member into the body lumen such that the additional obstruction is positioned between the distal end of the treatment member and the expanded distal end of the outer member;
expanding the first expandable member on the treatment member distal end using a contrast solution;
manipulating the expanded first expandable member while monitoring the first expandable member using external imaging until the first expandable member is disposed within the additional obstruction; and
expanding the second expandable member on the treatment member adjacent the first expandable member to dilate the additional obstruction.

5. The method of claim 1, wherein:
the guidewire has an outer portion over an inner portion,
the method further comprises removing, after introducing the flow restoration apparatus over the guidewire into the body lumen, the outer portion of the guidewire while an inner portion of the guidewire remains in the body lumen, and
introducing the treatment member through the first lumen of the outer member and into the body lumen comprises introducing the treatment member over the inner portion of the guidewire through the first lumen of the outer member and into the body lumen.

6. The method of claim 1, further comprising coupling one or more fluid or aspiration sources to the flow restoration apparatus, such that at least one of the one or more fluid or aspiration sources is in fluid communication with the first lumen.

7. The method of claim 6, wherein the one or more fluid or aspiration sources comprise a source of inflation media, a source of vacuum, a source of a diagnostic agent, or a source of a therapeutic agent.

8. The method of claim 7, wherein the one or more fluid sources comprises a source of inflation media, and wherein expanding the distal end of the outer member from the collapsed configuration to the tapered, expanded configuration comprises delivering inflation media from the source of inflation media to an interior of the distal end of the outer member.

9. The method of claim 1, wherein the treatment member comprises a lumen, and wherein the method further comprises coupling one or more fluid or aspiration sources to the flow restoration apparatus, such that at least one of the one or more fluid or aspiration sources is in fluid communication with the lumen of the treatment member.

10. The method of claim 9, wherein the one or more fluid sources comprise a source of inflation media, and wherein expanding the first expandable member on the treatment member distal end comprises delivering inflation media from the source of inflation media to an interior of the first expandable member.

11. The method of claim 1, wherein the distal end of the outer member comprises an annular expandable member comprising an outer annular membrane configured to expand to the tapered configuration.

12. The method of claim 11, wherein the annular expandable member further comprises an inner annular membrane, wherein a distal end of the outer annular membrane and a distal end of the inner annular membrane are bonded.

13. The method of claim 12, wherein a proximal end of the outer annular membrane is spaced apart from a proximal end of the inner annular membrane along the outer member.

14. The method of claim 1, wherein withdrawing the treatment member into the first lumen of the outer member comprises withdrawing the treatment member into the first lumen of the outer member such that the first expandable member is received within the first lumen of the outer member.

15. The method of claim 1, wherein the distal end of the inner member is configured to capture part of the distal end of the outer member while the flow restoration apparatus is introduced into the body lumen.

16. A method for treating a body lumen, the method comprising:
introducing a guidewire into the body lumen, the guidewire having an outer portion over an inner portion,
introducing a flow restoration apparatus over the guidewire into a body lumen, the flow restoration apparatus comprising an outer member defining a first lumen, and an inner member disposed within the first lumen of the outer member;
removing the outer portion of the guidewire while an inner portion of the guidewire remains in the body lumen;
expanding a distal end of the outer member from a collapsed configuration to a tapered, expanded configuration, such that a diameter of a distal opening of the outer member is substantially equal to an inner diameter of the body lumen;
withdrawing the inner member from the first lumen of the outer member, thereby leaving the outer member with its distal end in the expanded configuration disposed within the body lumen;
introducing a treatment member over the inner portion of the guidewire through the first lumen of the outer member and into the body lumen, such that material within the body lumen is positioned between a distal end of the treatment member and the expanded distal end of the outer member;
expanding a first expandable member on the treatment member distal end; and
withdrawing the treatment member into the first lumen of the outer member such that the material in the body lumen is also withdrawn into the first lumen of the outer member.

17. The method of claim 1, wherein the shaft comprises an inner layer and an outer layer surrounding the inner layer.

18. The method of claim 17, wherein the inner layer comprises a substantially inelastic material including one or more slots configured to elastically deform to cause radial expansion of the shaft.

19. The method of claim 17, wherein the outer layer comprises one or more elastic materials that prevent fluid from passing into the first lumen.

20. A method for treating a body lumen, the method comprising:
   introducing a flow restoration apparatus into a body lumen, the flow restoration apparatus comprising an outer member having a shaft defining a first lumen, and an inner member disposed within the first lumen of the outer member, the shaft having a distal end configured to radially expand, a distal end of the inner member extending distally of the distal end of the outer member and configured to capture part of the distal end of the outer member;
   expanding the distal end of the outer member from a collapsed configuration to a tapered, expanded configuration while the inner member is within the first lumen of the outer member, such that a diameter of a distal opening of the outer member is substantially equal to an inner diameter of the body lumen;
   withdrawing the inner member from the first lumen of the outer member, thereby leaving the outer member with its distal end in the expanded configuration disposed within the body lumen;
   introducing a treatment member through the first lumen of the outer member and into the body lumen such that material within the body lumen is positioned between a distal end of the treatment member and the expanded distal end of the outer member;
   expanding a first expandable member on the treatment member distal end; and
   withdrawing the treatment member into the first lumen of the outer member such that the material in the body lumen is also withdrawn into the first lumen of the outer member, the withdrawal of the material in the body lumen causing radial expansion of the shaft.

* * * * *